United States Patent [19]

Johnson et al.

[11] 4,066,412

[45] Jan. 3, 1978

[54] AUTOMATIC CLINICAL ANALYZER

[75] Inventors: Donald R. Johnson, Wilmington; Richard G. Nadeau; Gerrit Nieuweboer, both of Claymont, all of Del.; William L. Truett, Blackwood, N.J.

[73] Assignee: E. I. Du Pont de Nemours and Company, Wilmington, Del.

[21] Appl. No.: 753,197

[22] Filed: Aug. 16, 1968

Related U.S. Application Data

[63] Continuation-in-part of Ser. No. 545,494, April 26, 1966, Pat. No. 3,476,515.

[51] Int. Cl.² ............. G01N 33/16; G01N 21/24
[52] U.S. Cl. ........................... 23/253 R; 23/259
[58] Field of Search ............ 23/230, 253, 259, 292; 206/47

[56] References Cited

U.S. PATENT DOCUMENTS

| 2,797,149 | 6/1957 | Skeggs | 23/253 X |
|---|---|---|---|
| 3,266,298 | 8/1966 | Whitehead et al. | 23/253 X |
| 3,476,515 | 11/1969 | Johnson et al. | 23/230 |
| 3,477,822 | 11/1969 | Hamilton | 23/253 |
| 3,497,320 | 2/1970 | Blackburn et al. | 23/292 X |
| 3,504,376 | 3/1970 | Bednar et al. | 23/230 R |

Primary Examiner—R.E. Serwin

[57] ABSTRACT

An apparatus for automatically performing analytic procedural steps on a fluid contained in a disposable deformable test pack. The apparatus consists of a means for filling the test pack with sample fluid, a means for controlling the environment of the test pack, a means for initiating reactions within the test pack, a means for analyzing the fluid in the test pack, and a transport means designed to hold the test pack and to transport it between the various operating stations. Associated circuitry combining method switchng and control logic make the operation of the instrument fully automatic.

60 Claims, 8 Drawing Figures

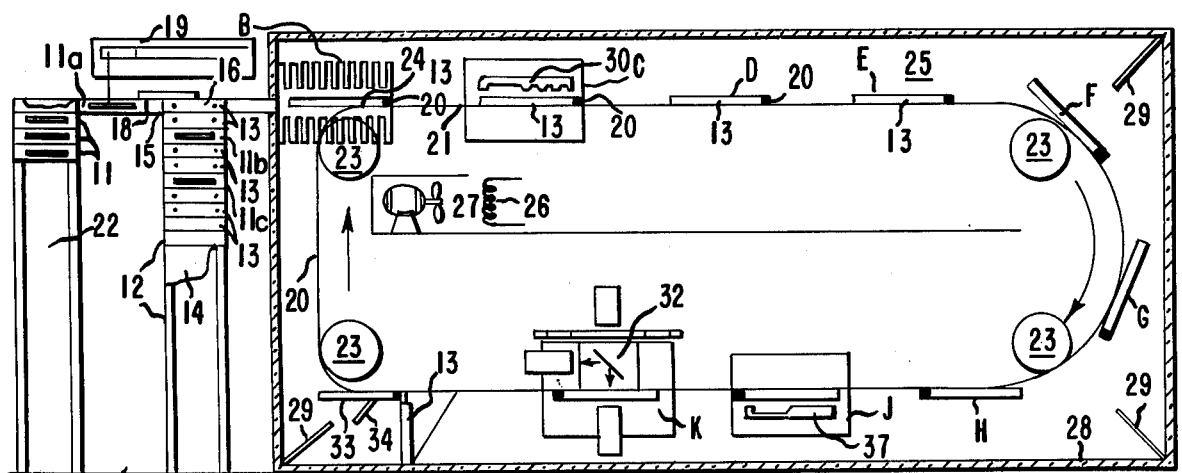
FIG. 1
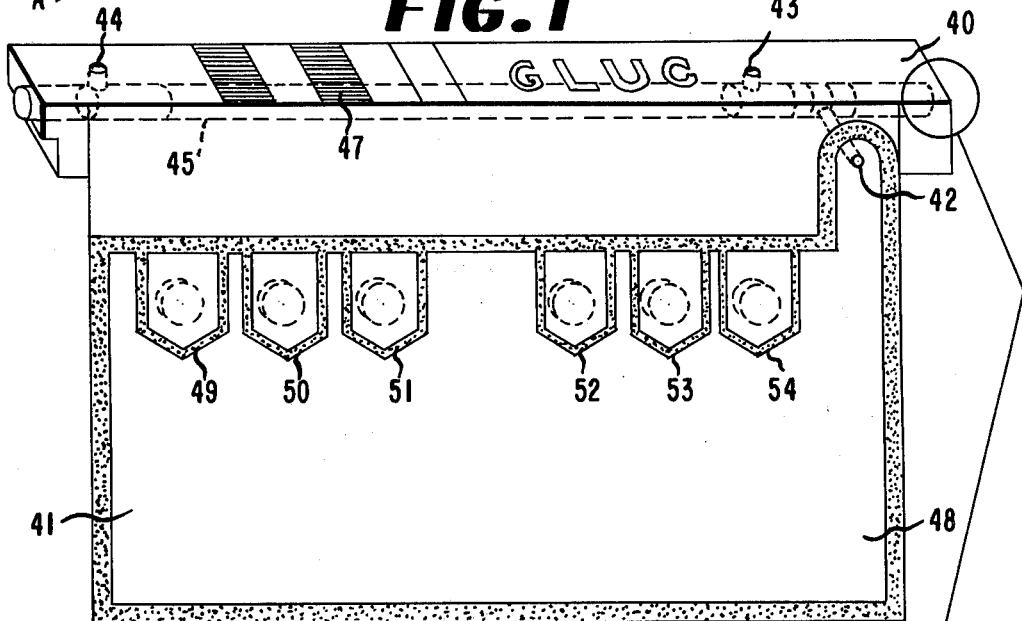
FIG. 2B
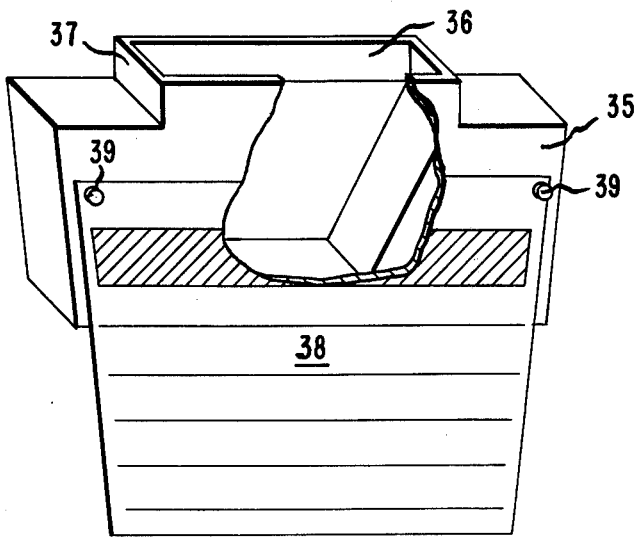
FIG. 2A
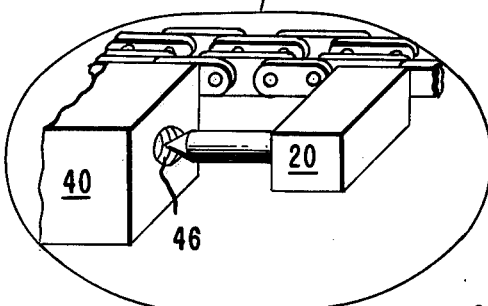
INVENTORS
DONALD R. JOHNSON,
WILLIAM L. TRUETT
RICHARD G. NADEAU
GERRIT NIEUWEBOER
BY
ATTORNEY

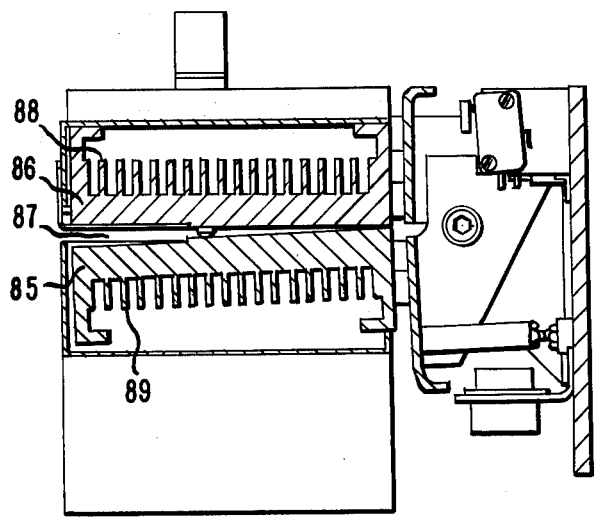
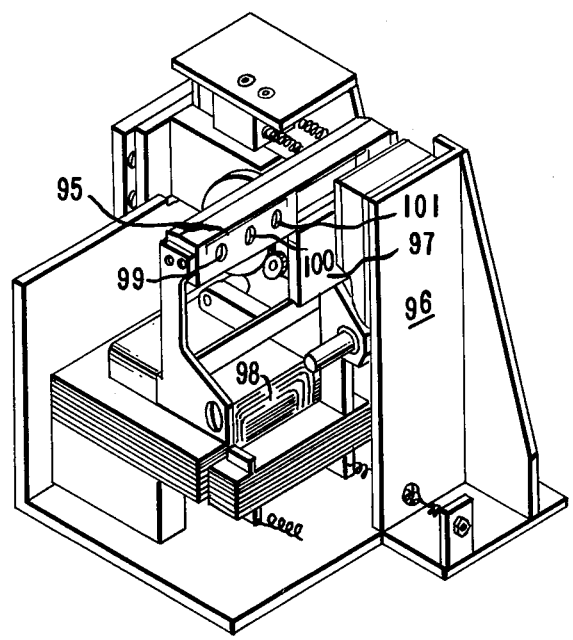
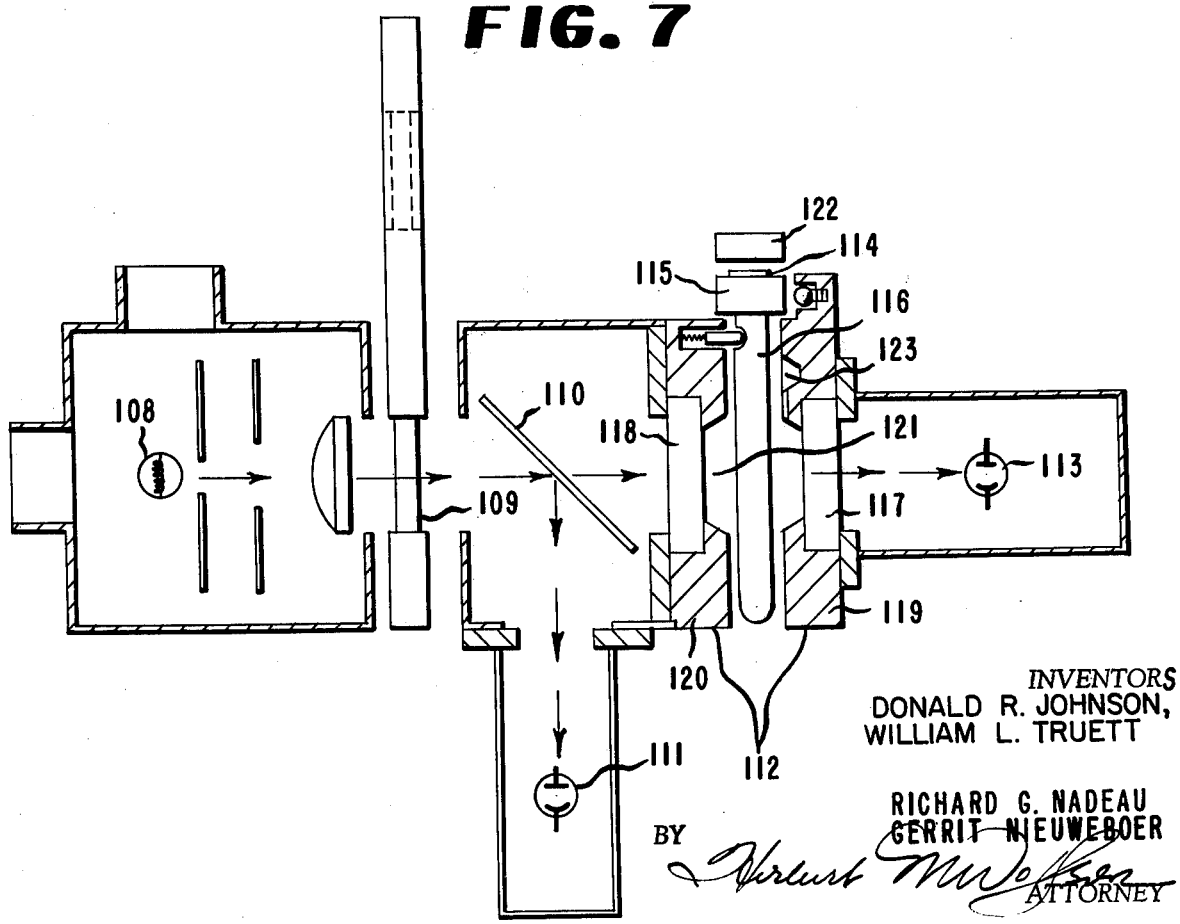

AUTOMATIC CLINICAL ANALYZER

CROSS REFERENCE TO RELATED APPLICATIONS

This invention is continuation-in-part of copending application Ser. No. 545,494 now U.S. Pat. No. 3,476,515 filed on Apr. 26, 1966 entitled Analytic Test Pack and Process for Analysis by D. R. Johnson, et al (assigned to the assignee of the present application). It is also related to the subject matter of application Ser. No. 753,199 now U.S. Pat. No. 3,612,360 filed the same day as this invention entitled Apparatus and Method for Fluid Handling and Sampling by W. J. Ambrose et al (assigned to the assignee of the present application) since the sampling apparatus described and claimed therein can be used as an element of the instant invention. Finally it is related to the subject matter of application Ser. No. 753,200 filed the same day as this invention entitled Apparatus and Method for Performing Photometric Analysis by E. P. Carter (assigned to the assignee of the present application) since the photometric system described and claimed therein can be used as an element of the instant invention. These cross references are merely intended to illustrate and not to restrict the scope and/or use of any of these inventions.

BACKGROUND OF THE INVENTION

Many routine laboratory tests have been developed to the stage where they can be performed by automation. This is an advantage in areas such as clinical testing where automation can profitably be used to free technicians for other tasks, and where automation insures a more accurate analysis than was previously possible by reducing the human error involved. This trend towards automation has led to the development of a number of completely automatic analytic instruments, which are now in use, primarily in clinical areas and primarily for analyzing reaction rates in fluids.

The most fully automatic of these instruments are, with rare exception, principally sampling systems where ingenious methods are employed to remove the fluid to be tested from its container and to deliver it to a cuvette, where it is mixed with the proper reagents. The cuvette is then positioned in the analysis stage, and the fluid in it analyzed by conventional means. In one such instrument the sample fluid and reagents are supplied to the cuvette through a single tube by the pumping action of a proportional pump. The different fluids are separated from one another by air bubbles, which also act as a means for cleansing the tube so that the fluids will not become contaminated. In another instrument the fluid to be analyzed is deposited on a porous tape, and the reagents are supplied from another porous tape by bringing the two into contact from a specified time interval. The tape is then used to present the mixture to the analysis stage.

The present invention is an integrated instrument, based on the use of a deformable test pack. It incorporates not only a system for sampling the test fluid and introducing it without contamination into the test pack, but also various other preparational and operational stages through which the sample cell proceeds until the analysis is complete. It is designed to be fully automatic and, therefore, unusually simple to run; to allow easy selection of the type, number, and order of analysis performed on each sample; and to be immediately operable without waste of time or material in startup or shutdown. The entire reaction and analysis of that reaction takes place in a sealed test pack which is identified upon entering the instrument. The test results are converted automatically to the proper units, and are printed on a separate report sheet for each sample.

Certain of the elements of the instrument such as the deformable test pack, the sampling system, and the photometric system, which are of broad application, are the subject of separate patent applications, mentioned above. The instant invention is concerned with those novel aspects of the instrument which make it a fully automatic, integrated analysis system. It is concerned with the way in which the test pack is presented to the sampling system, in such manner that future operations upon the test pack are predetermined from that stage on, and with the way in which the test pack is transported from the filling stage, through various preparational and operational stages, to the analysis stage and from there to disposal.

The advantages of the instrument are to be found in the fact that since the sample fluid is contained along with the reagents in a closed test pack, the possibility of contamination is reduced, as is the possibility of confusion due to improper test identification. The sample and test are positively identified, on the test pack, and the type of tests to be run can be readily interchanged. Cleansing is no longer a problem since the test pack is inexpensive enough to be disposable; and, since the test pack is deformable, preparation and analysis of the fluid contained therein is particularly easy.

The operation and advantages of the instant invention can be seen by reference to the following figures, wherein:

FIG. 1 is a schematic diagram of one embodiment of the integrated automatic analytic instrument;

FIGS. 2A and 2B are diagrams of possible embodiments of a sample container and test pack, respectively, which can be used in this instrument;

FIG. 5 is one embodiment of a preheater which can be used as part of the environmental control system used in this instrument;

FIG. 6 is one embodiment of an element of the reaction originating means which can be used in this instrument; and FIG. 7 is one embodiment of an analysis means which can be used in this instrument;

DISCUSSION OF THE FIGURES

Figure 3:
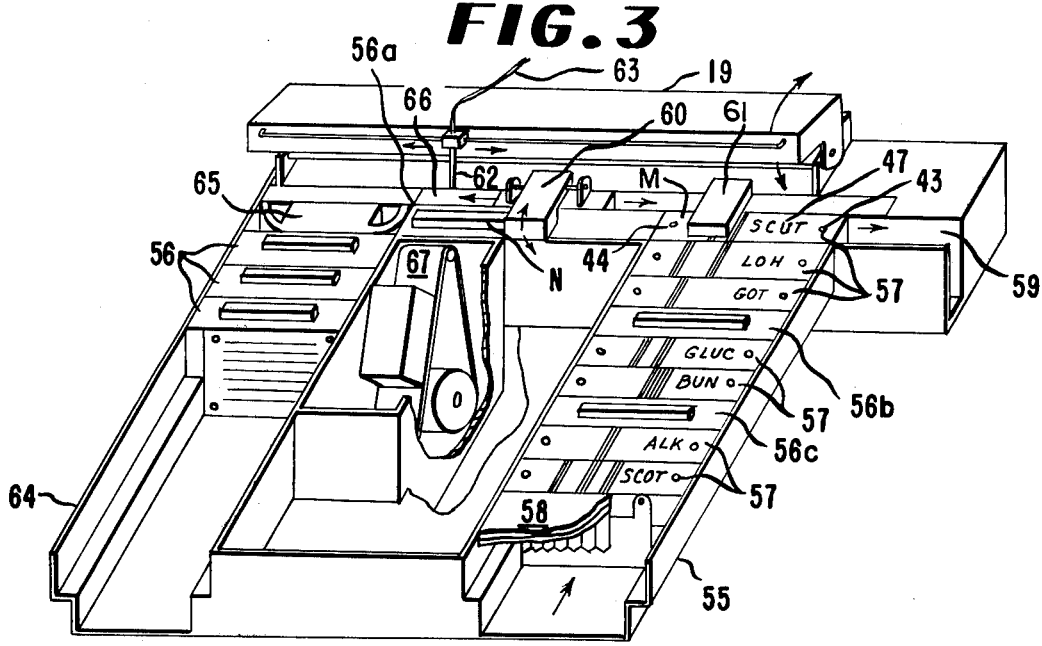
FIG. 3 is a diagram of one embodiment of a sample container and test pack feeding means which can be used in this instrument.

FIG. 1 is a schematic diagram of an integrated automatic analytic instrument. In this figure a number of disposable plastic sample containers 11 containing the fluid to be tested are placed in the input tray 12 of the sample container and test pack feeding means A. Each sample container is followed by one or more test packs 13, depending on the number of specific tests which are to be performed on each sample. Each test pack is designed for use in one test, and its juxtaposition with a particular sample container insures that that particular test will automatically be performed on the sample. The presence of the test pack determines the test to be run. If no test pack follows the sample contaner, the machine will stop, or go into a standby stage. A spring loaded pack follower 14, pushes the sample container and pack set towards the positioning track 15 at the exit of the input tray, so that the first sample container 11a rest in the positioning track. This portion of the positioning track also serves as the filling station 16 for the test pack during the fill cycle. The first sample container 11a is then moved from the input tray 12 to the sampling position 17 by a shuttle 18 which travels with a linear cyclic motion between the right and left side limits of the positioning track. The shuttle begins its cycle from the right side limit and moves towards the left side limit, passing the input tray. If the exit of the input tray contains a sample container, the shuttle will engage the sample container as it passes the tray, and push the sample container along the positioning track into the sampling position. The shuttle will then remain in this position. If the tray contains a test pack, the shuttle is adapted to pass the test pack and move to the left side limit where it will remain. If the tray is empty, the shuttle is adapted to move to the left side limit, and then reverse its direction returning to the right side limit before it stops. At this point the instrument will go into a standby position.

After the first sample container 11a has been moved to the sampling position, the first test pack following it will advance to the filling position 16 for the test pack. The filling means 19 then aliquots sample fluid from the sample container 11a to the test pack 13. At the end of this filling cycle, the shuttle moves from its rest position, at the left side limit, to the right side limit, again passing the input tray. In this portion of its cycle, the shuttle makes contact with the header of the test pack and upon engaging the test pack, the shuttle moves it along the positioning track towards the first operating station B of the transport means 21. The shuttle is then in position to repeat the feed cycle. A second test pack is advanced to the filling station, and is in turn supplied with the fluid to be sampled from the same sample container 11a as was used to supply the first test pack. After it has been filled, the second test pack is then moved on to the transport means, and the procedure repeats itself for as many times as there are test packs following a specific sample container in the input tray. In this manner, a number of tests can be run on the same sample simply by placing the desired test packs behind the sample container in the input tray. When instead of a test pack, a new sample container 11b is presented to the positioning track, the shuttle moves it towards the sample position. In order to make room for this new sample container 11b in the sampling position, the expended sample container 11b is ejected from the sample position into the sample return chute 22. The first of the test packs accompanying the second sample container 11b is then presented to the filling station, and the procedure described above is repeated.

The transport system 21 in this embodiment is a continuous chain arranged in an elongated circular pattern. At periodic intervals along the chain there are packs carrying fixtures 20 which are designed to accept and hold the test packs when they are presented to the transport means by the shuttle. In this embodiment, these fixtures are pins, but any suitable fixture could be used. The continuous chain is mounted on sprockets 23 which are driven by an index motor, not shown. In this particular embodiment the index motor is programmed so that after remaining in position for a set time interval the chain carrying the pack will be moved the periodic distance between carrying fixtures. The time required for the indexing motor to move the pack from one station to the next, plus the time that the test pack remains at the station, is referred to as the machine cycle time, and determines the maximum speed of the machine. This time can be varied. At the beginning of each machine cycle, then, a new test pack is moved from the filling position to the first station of the transport means. At periodic distances along the transport means, corresponding to the position at which the test pack is delayed, there is an operating station at which the test pack is subjected to some step in the analytic procedure. The length of time required to perform the longest of these steps determines the time during which the test pack must remain at that station, and dictates the machine cycle time.

In this embodiment a preheater 24, which is part of the environmental control means, is located at the first operating station B. The test pack illustrated in FIG. 2 contain reagents, and is generally kept under refrigeration. Since temperature will effect reaction rates, it is necessary for the analyzer to heat the pack and its contents to a specified controlled temperature. Initially this is accomplished by a preheater, which in this instance is used to heat the pack and its contents to the desired temperature. In another embodiment, the preheater 24 occupies two operational stations in the instrument, and the heater consists of two heating stages. The first stage is a pair of heavy metal blocks, heated electrically, which are brought together with the test container between them. They raise the temperature of the container rapidly to the desired range. The next stage consists of two thin metal blocks with heating fins heated by hot air from a blower. This stage acts as the temperature fine control. Once the pack leaves the preheater, it is kept at the operative temperature by the remainder of the environmental control system. In this embodiment the remainder of the environmental control system is a controlled temperature chamber 25. All of the stations of the automatic analyzer, except for the pack feeding means A and the filling station 19, are contained within the controlled temperature chamber. The temperature within the chamber is maintained constant, in this case at 37° C., by employing a thermistor in a feedback arrangement to control the power supplied to a wire grid 26 used as a heating element. The grid is located at the inlet of a circulating fan 27 so that heated air can be continuously circulated around the chamber, which is itself insulated from the outside by a suitable temperature insulating material 28, such as Styrofome ®. Baffles 29 are provided within the chamber to give a circular pattern to the air flow.

Once the test pack has reached operating temperature, it is moved to the second operating stage C, which in this instance is part of the reaction originating mechanism. As will be described below, this particular device 30, called breaker-mixer I, is designed to release certain of the reagents contained in the test pack, and to mix them with the sample fluid. After the first series of reagents is introduced into the sample fluid the test pack is moved through a plurality of operating stations, D, E, F, G and H, called delay stations, which are provided to allow the reaction to proceed. If the test is a complicated one, more reagents than were initially released may be required, so another element of the reaction originating system, called breaker-mixer II 31, is provided at station J to release other reagents from their storage place in the test pack into the sample fluid. Although breaker-mixer II, in this embodiment, is positioned at station J, directly before the analysis station K, the position of breaker-mixer II can be varied. It can be moved to any one of the preceeding delay stations, so that there will be at least one delay station between it and the analysis position if desired.

Eventually, the test pack is presented to the analysis station K, which in this embodiment is a photometer 32. Generally it is a reaction rate which is of interest, and this is measured, as will be described below, by measuring the change in optical density of the fluid during a certain time interval. The information from this measurement is fed to a readout system, not shown, and the test pack moves on to station L, wherein an expended pack accumulator is located. In this embodiment, the expended pack accumulator comprises a pack stop 33, designed to dislodge the analytic pack from the pack carrying fixture, a guide chute 34, and a waste can, not shown, into which the expended, disposable, test pack drops.

FIG. 2A is an illustration of one embodiment of a sample container which can be used in the automatic instrument described above. It consists of a header 35, made from some easily molded or machined material, such as Styrene ®. The header contains a depression 36 in which the sample fluid is contained. The volume of this depression depends on the amount of sample fluid required in all of the test to be run on the sample. It is, therefore, dependent on the efficiency of the instrument. In this instrument a capacity of 4 ml. is sufficient. Optionally, the header can also have a protrusion 37, designed to be engaged by the shuttle of the feeder, suitably located so that the shuttle can easily move the sample container to the sample position. In this illustration, the protrusion is an integral part of the header, and forms the lip of the depression into which the sample fluid is deposited, but the type and position of the protrusion depends upon the design of the machine. A simple spike inserted into the header at the appropriate spot would serve the same purpose. Optionally, this protrusion can be eliminated and the height of the header itself can be increased to the point where the shuttle will engage the whole header and not just the protrusion. The shape of the sample container is such as to facilitate its positioning within the input tray, the positioning track, and the expended sample container tray of the feeder.

The header of the sample contaner is also adapted to contain an identification card 38, which can be separated from or be part of the header. In one embodiment the identification card is a slip of acetate on which the sample information can be written in lead pencil. This slip is attached to the sample container header by pressing circular holes in the slip onto cylindrical tabs 39 on the header. Information concerning the test written on the identification card can be transferred to a light sensitive readout tape, in a manner described below, which upon completion of the test will also contain the analysis data. The transfer occurs every time a test pack is moved from the filling position to the transport means. In this way, once the proper sample is put in the sample container and the proper identification is made on the identification card, the results of the test are automatically correlated on the readout tape with the proper sample identification. This is accomplished by advancing the readout tape, with the sample identification contained on it, in increments such that the number of steps it takes to arrive at the final readout position is automatically set to correspond to the number of steps the analytic pack, associated with the test, takes to arrive at the readout station.

FIG. 2B is an illustration of one embodiment of a test pack which can be used with the automatic instrument described above. This pack is the subject of patent application Ser. No. 545,494. This pack consists of a header 40 which is similar in shape to that of the sample container so that both can fit in the same input tray of the feeder. From this header is suspended a deformable pouch 41, made from a strong material transparent to the particular radiation involved in the analytic procedure, and resistant to the chemicals employed. Surlyn ® has been found to be a suitable material. The pouch is sealed around its perimeter and connected to the header by an opening 42. The top of the header has two openings 43 and 44. These openings can be covered with a rubber dam so that the whole system is closed. The sample fluid could then be injected into the test pack through one of these openings by a hypodermic needle inserted through the dam before the injection is made. Opening 43 leads directly to the pouch through opening 42 so that sample fluid deposited in opening 43 will flow directly into the pouch. Opening 44 is separated from opening 42 by a separation chamber 45 so that sample fluid deposited in opening 44 will have to pass through the separation chamber before it reaches the opening 42 into the pouch. This separation chamber can contain a filter, a gel column, an ion exchange resin or any other analytical element required in the analysis. Depending upon the test required, the sample fluid can be deposited into either of the openings.

The header can optionally contain a protrusion much like that on the sample container, so that the shuttle can selectively engage and position the test pack in the proper place, and finally move it on to the pack carrying fixture. Optionally, no protrusion need be supplied. In this case the selectively of the shuttle would be supplied by the difference in height of the two headers. In the figures, protrusions are shown only on the sample container so the test packs can be differentiated from the sample containers. The header of the test packs also contains an opening 46, in its end, which is adapted to fit on carrying pin 20, attached to the transport chain as shown in the insert for FIG. 2B, so that the test pack can be engaged and supported by the pack carrying fixture. Finally the header contains visual identification symbols and identification marks 47 which identify the type of test for which the pack is designed. The identification symbols are generally an abbreviation of the test to be performed, so that the operator can visually identify the test. The identification marks are for the machine to interpret. They can be light and dark spaces on the header which can be read photometrically; they can be magnetic in nature; they can be raised portions on the header which can be read mechanically by a feeler gauge; or they can be any other suitable identification means. The identification marks can be used to program the analytic procedures which follow as will be shown below. The pouch 41 is divided into a number of chambers. One of these 48 is the reaction chamber. The other chambers contain reagents and are separated from the reaction chamber by seals 49 through 54 which can be ruptured by exerting pressure on them. It is these seals which will be broken by the breaker-mixers as described below, so that the reaction can begin.

FIG. 3 is a diagram of one embodiment of the sample container and test pack feeding system which can be used to present the sample containers and test packs to the proper position for fluid transfer, and for presentation to the operational stages of the analytic instrument. In this embodiment, the input tray 55 contains a number of sample containers 56, each followed by at least one analytic pack 57. They are held in position by a spring loaded pack follower 58 which forces the first item in the input tray into the presentation position M in the positioning track 59. In the figure, the shuttle 60 has engaged the first sample container 56a and has moved it to the sample container position N in the positioning track 59. The first test pack following the sample container is in the presentation position M, which in this embodiment is also the filling position. There is an identification means, 61 which photometrically decodes the identification mark 47 on the test pack, and programs the filling means 19 as to the amount of fluid to be transferred from the sample container 56a to the test pack, and as to which opening 43 or 44 into which the fluid is to be deposited. The probe of the filling means 62 is moved into position over the sample container 56a, and a predetermined amount of fluid is removed from the sample container by suction provided by a pumping system at the end of tube 63. A buffer solution from an external source can be added to the sample fluid, as described below, and the two fluids deposited in one of the openings of the test pack by the filling means which has moved to position the probe over the proper opening in the test pack. The probe can be moved to either side to be positioned over either the sample container or either opening of the test pack, and it can be moved up and down in a rocking motion so that it can be inserted either into the sample fluid or the proper opening in the test pack. This motion is programmed by the circuitry associated with the identification means discussed above. After the test pack has been filled, the shuttle is moved to engage the test pack. The shuttle moves back and forth between the right side limit and left side limit of the positioning track. It also has a motion which allows it to selectively engage either the sample container or the test pack. The motion of the shuttle can be an up and down motion, so that, if the header of the sample cup is higher than that of the test pack, the shuttle could be raised to miss the test pack and engage only the sample container and lowered to engage the test pack on the return portion of the cycle. Optionally, any other motion which will selectively engage the sample cup and the test pack can be used. In any case, the shuttle moves the test pack to engage the pack carrying fixture on the transport means. The shuttle then returns through the presentation position. If another test pack is in that position, the shuttle will pass over it, and return to the left side limit. The second test pack is then filled by sample container 56a. If, however, another sample container is in the presentation position, the shuttle will pass over it, and return to the left side limit. The second test pack is then filled by sample container 56a. If, however, another sample container is in the presentation position, the shuttle will engage the sample container and move it toward the sample position. This motion will trigger ejection of sample container 56a into the expended sample container chute 64. This can be done either directly, or indirectly by allowing sample container 11b to push sample container 11a further to the left, from which position it is then ejected into the expended container chute by a spring loaded ejection device 65. The sample container position also contains a light source 66, positioned behind the sample container in such manner that it will shine through the identification card attached to the sample container and impinge on the light sensitive readout tape 67. This will transfer the information on the card to the light sensitive readout tape.

Figure 4:
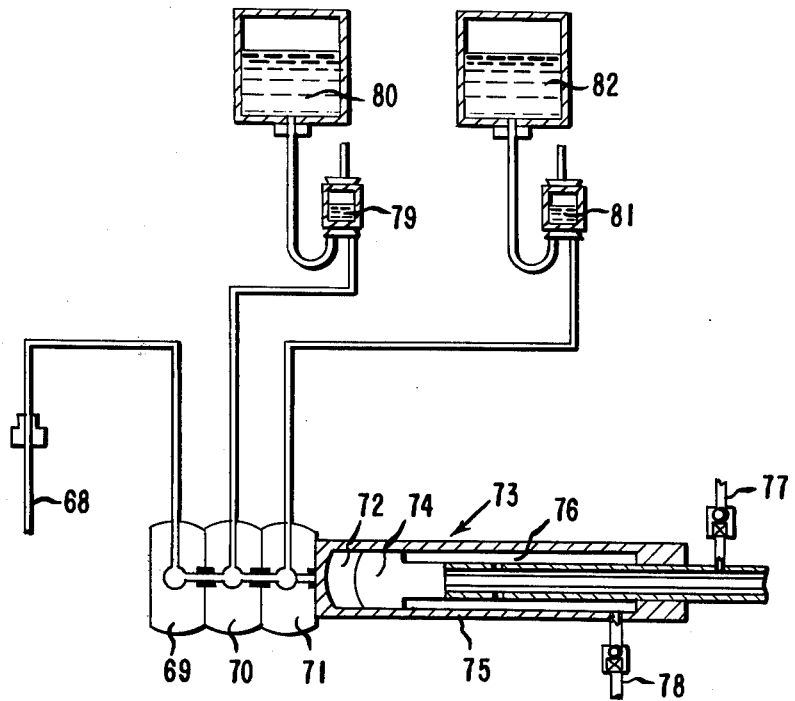
FIG. 4 is one embodiment of a filling means which can be used in this instrument.

FIG. 4 is a diagram of one embodiment of a filling means which can be used with the automatic instrument described above. It consists of a probe 68, which is mounted on the movable portion of the filling means 19 shown in FIG. 3. In this instance the probe is a hypodermic needle which can be inserted into the rubber dam closing the openings 43 and 44 of the test pack shown in FIG. 2B. The probe is connected to an intake-output valve 69, and through a plurality of intake valves 70 and 71 to the pump chamber 72 of a pump 73. The pump is of the piston 74 in a cylinder 75 type, which is motivated by a precision motor, not shown, programmed to move the piston so that the volume in the pump chamber can be changed in 20 microliter increments with an accuracy of 0.5 microliters. The pump is designed so that the motion of the piston will draw a cleansing fluid into the area behind the piston 76, through valve 77, and expel the cleansing fluid through valve 78; automatically cleansing that portion of the pump on each cycle. Intake valve 70 is connected through a de-bubbler 79 to a source of secondary fluid 80, such as a buffer solution, and intake valve 71 is connected through a de-bubbler 81 to a source of cleansing fluid 82. In this manner a buffer solution can be drawn into the pump chamber, and sample fluid can be drawn into the probe. Both fluids can then be deposited into the test pack. After the fluids have been dispensed from the pump, a cleansing fluid can be drawn into the pump chamber 72, and dispensed into a waste bottle, not shown, through the probe cleansing that portion of the system not cleaned by the fluid drawn in through intake valve 77. The exceptional features of this system, which are the subject of patent application, Ser. No. 753,199, are found in the construction of the intake valve which is designed so that it will pump less than a microliter of fluid when it operates; and of the intake-output valve which is designed to aspirate into the body of the valve any liquid remaining on the lip of the probe, with no more motion than is inherent in the operation of the valve itself and with no change in the physical dimensions of the valve, so that no excess fluid will remain on the lip of the transfer probe to contaminate or dilute the sample fluid during the next transfer of sample fluid to a test pack. This latter is accomplished by designing the valve stem and closing means of the valve so that upon the movement of the closing means, to open or close the valve, the free volume within the valve chamber will decrease, by a precise amount, causing a suction at the lip of the transfer probe which aspirates the excess fluid.

FIG. 5 is a diagram of one embodiment of a preheater which can be used in this instrument. It consists of two jaws 85 and 86, forming a chamber 87, which close around the test pack after it has been inserted on the pack carrying pin of the transport means by the feed shuttle. The exhaust outlet of a blower, not shown, forces heated air through the preheat chamber and heats the chamber jaws. When the pack enters the chamber, the jaws are brought together, gently squeezing the pack and transferring heat to the pack. The blower is part of the controlled temperature chamber heating system 26 and 27, shown in FIG. 1. The preheater jaws open during the period when the transport system is moving. To facilitate heat transfer to the jaws, the jaws have an increased surface provided by fins 88 and 89, as shown. Optionally, another preheater stage can be included before this stage, comprising two heavy metal blocks, heated electrically, which close around the test pack and bring it up rapidly to the desired temperature range. The preheater, discussed above, would then be used as a fine control on the temperature of the pack.

FIG. 6 is a drawing of one embodiment of a reaction originating means which can be used in this instrument. To begin the initial reaction, the initial reagents must be removed from their storage position in the test pack, and mixed with the buffer-sample solution in the reaction chamber 48 of the pack. This is accomplished by breaker-mixer I, located at station C of FIG. 1, and illustrated by FIG. 6. This breaker-mixer is designed to rupture the seals 49, 50 and 51, shown in FIG. 2B, while protecting the seals 52, 53 and 54. It consists of a protector bar 95, a back plate 96, a rupture-mixing platen 97, and an electromagnet 98. The protector bar contains three cylindrical indentations 99, 100, 101, designed to protect rupturable seals 50, 51 and 52. In operation, the protector bar is driven shut across the top of the pack, against the back plate, by a force supplied by a motor. The bottom portion of the pack 48 is then squeezed between the platen and the back plate, and the fluid in the reaction chamber 48 is forced upward, against the rupturable seals 49, 50 and 51, rupturing them. The fluid enters the reagent containing cells, dissolving the contents. The platen 97 is then partially withdrawn, and the electromagnet is pulsed causing the platen to oscillate in and out. This creates a mixing action inside the pack. After a certain time interval, the mixing action is stopped, and the protector bar and platen are withdrawn so that the pack is ready to move on.

Breaker-mixer II, which is the second half of the reaction originating means, is designed to release the remaining reagents in the pack into the buffer-sample solution. It is similar to breaker-mixer I, as shown in FIG. 6, except the protection bar does not contain the cylindrical indentations to protect the seals. Instead, the protector bar is flat over the area of seals 49, 50 and 51 so that none of the fluid will enter the cells with the ruptured seals. All of the fluid is used to rupture seals 52, 53 and 54. A mixing step is also included. Generally, those reagents which will induce fast reactions are released by breaker-mixer II, and those that induce slow reaction are released by breaker-mixer I. If the reaction is extremely rapid, the activation of breaker-mixer II can be delayed until near the end of the machine cycle.

FIG. 7 is a diagram of one embodiment of an analysis system which can be used in the instrument. In this instance it is a photometer. It comprises a light source 108 which emits radiation of the proper frequency, a filter 109, a beam splitting mirror 110, a regulating photocell 111, a cell forming means 112, and a measurement photocell 113. The radiation from the light source, which in this embodiment is a quartz iodine lamp, is collimated and focused, and then passed through the filter 109. The filter can be selected, the selection being accomplished by using a filter wheel with a plurality of filters. Which filter is used will depend on the particular reaction rate being measured. The particular filter used can be selected by the identification mark 114, contained on the header 115 of the test pack 116. Since the intensity of the light should not vary with the filter used, a beam splitter and regulator photocell are used to monitor the light passing through the filter. Approximately 10 percent of the light incident on the mirror 110 is reflected to the photocell 111, which in conjunction with a feed back circuit, not shown, maintains the intensity of the light at the mirror constant, by varying the power supplied to the light source. The remaining 90 percent of the light passes through the analytic pack and arrives at the measurement photocell 113. The novel feature of this photometer system, which is the subject of application Ser. No. 753,200, is the cell forming means 112, which consists of two flat quartz windows 117 and 118, recessed into two jaws 119 and 120 in such manner that when the jaws are brought together on the deformable portion of the test pack, the fluid in the pack squeezes the walls of the pack into the shape of the recess in the jaws, forming a sample cell in the region 121. The photometer is designed so that the dimensions of the sample cell are precise and reproducible, and also designed so that substantially all the fluid in the test pack is contained in the sample cell. This effective use of the fluid increases the sensitivity of the photometer. Because the windows are flat, the deformable pouch will be deformed into a sample cell with substantially flat walls. If, in addition, a contact fluid applicator is included to coat the surface between the pouch and the windows with a contact fluid, this contact fluid will stabilize the recesses between the pouch and the window, formed by imperfections in the film from which the pouch is made, which would otherwise change dimensions during transmission measurements enough to introduce a substantial change in reflection and, therefore, a substantial error. In this embodiment, the cell forming means contains an additional recess, connected to the cell forming chamber by a narrow channel. This recess 123 is a pressure relief chamber, designed to equalize the pressure in the cell forming recess so that small variations in the amount of fluid in the pack will not cause variations in the size of the cell forming chamber.

Once the sample container, properly identified and containing the sample fluid, is placed in the input tray, followed by the desired test packs, the instrument will automatically perform the proper operational steps, and the results of the test will be correleated with the proper sample identification. This is accomplished by an internal system of control logic and method switching. The control logic directs the operation of the pack handling system, the filling stations, the breaker-mixers, the photometer, the printer, the fluid metering system, the pack transport and the analog to digital converter associated with the readout. The logic sequencing is accomplished by a series of switches and photocells which detect component movement, or by internal timers which operate from a clock generator. The method switching provides a means of identifying the type of pack being processed, and of specifying the machine variables required for that test. Logic sequencing takes place at every step throughout the instrument. Method switching takes place at the filling station and at the photometer. The logic sequence circuits merely programs the operation of the instrument with reference to the time that the test pack and sample container remain at each station, and the order in which the machine is to perform its functions. This has been discussed above with reference to FIG. 1. The versitility of the instrument, however, can perhaps best be illustrated by a short discussion of the alternatives available through the method switching circuitry.

At the filling station, a photoreader, aided by a translator, identifies the test pack by decoding the identification marks on the header. Optionally, the reader can be a magnetic or a mechanical reader, but, in this embodiment, it is a series of photodiodes, activated by a light reflected through the light and dark spaces on the header. With the information received from this identification, the instrument determines the amount and type of buffer solution, if any, to be drawn into the chamber of the pump, the amount of sample fluid to be drawn into the probe, the amount of the sample-buffer solution to be injected into the test pack, and whether this solution should be injected directly into the reaction chamber of the test pack or into the reaction chamber through the separation column. Having made this determination, the logic control circuit programs the instrument to perform the necessary steps.

Logic sequencing, then, attends to the details of transporting the filled test pack through the instrument to the photometer. Test packs are kept in register so that method switching can allow variations in procedure, between the filling stage and the photometer, which are determined by the initial identification of the test pack. One such variation occurs at mixer-breaker II. For some rapid reactions, the introduction of the last reagents into the test solutions by the action of the breaker must be delayed. The order for this delay stems from the identification of the test made at the filling stage.

When the test pack arrives at the photometer, a second photoreader and translator redecodes the identification symbols and determines the analysis method. Since the packs are in register, this could have been determined from the first identification, but for convenience of operation, a second decoding stage is provided. At this stage, the proper filter and light intensity are selected. In addition to this, the type of reaction involved will dictate a decision as to certain measurement factors. The reason for these decisions can perhaps best be understood if preceded by a discussion of the operation of the photometer. The initial current generated by the photocell in response to the light transmitted through the sample cell is converted to a voltage signal which is fed into a log amplifier. This log amplifier voltage is compared with the sum of an offset voltage, which for purposed here, can be looked upon as a set voltage and a scaling voltage. The scaling voltage is the output of a scaling network, consisting of a resistor ladder network and 15 solid state switches, which are gated on and off by a 15-bit up-down counter. This network provides a variable voltage divider which allows a 8.192 volt reference voltage to be supplied to the summing input in increments of $8/2^{15}$ or 0.00025 volts. The sum of the offset voltage and scaling voltage is substracted from the log amplifier voltage, and the difference is fed into a discriminator-comparator which determines whether this voltage difference is greater than, equal to, or less than zero. If the difference is greater than zero, the comparator advances the up-down counter one count, which increases the scaling voltage by 0.00025 volts. If the difference is less than zero, the comparator decreases the counter one count, and the scaling voltage is decreased by 0.00025 volts. This process continues at a maximum rate of 7000 changes per second until the voltage difference balances to zero; at which time the counter content remains stationary. The process is repeated every time the log amplifier output changes. The comparator output is used to drive a decade counter. In this manner the voltage output of the photocell is converted to a digital response.

While the reaction is taking place in the test pack, and the transmission of the sample fluid is changing, the output of the log amplifier will be constantly changing as will the output of the decade counter. The readout system operates by allowing the comparator to balance the signal from the log amplifier and to display its output on the decade counter. When an initial balance has been obtained, a 16.8 second measuring cycle begins. During this time, the comparator continues to function, but the display of its output on the decade counter is suppressed. At the end of the measuring cycle, the comparator goes into a hold mode, and the decade counter displays its output. The binary coded decimal value of the output of the comparator at the beginning and at the end of the measuring cycle is fed to a printer, and a digital readout. The digital readout is for the benefit of the operator. The main output is an output which is printed on the light sensitive paper in juxtaposition with the sample identification, which was transferred to the paper at the filling stage.

At the photometer position, then, the method switching circuit informs the analog to digital converter of: the size scaling factor which will be appropriate for the particular reaction being run; what direction the counting will be in (i.e. will the transmission be increasing or decreasing), and the size of the counting step which will be appropriate. It also informs the printer what test is being performed, so that the test identification can be printed along with the sample identification and test results.

The instrument also contains an error detecting means. Errors can be detected at three stages in the operation. If the total sample and buffer volume is not correct for the particular test, this will be detected by the pump logic during the filling stage. If the cell is not formed properly in the photometer, a pressure check will divulge this. Finally, if the initial optical density of the sample fluid as determined by the photometer is not within prescribed limits, this will be detected. When an error is detected, an indication to this effect is printed on the readout and displayed on the digital readout.

What is claimed is:

1. An automated analytical apparatus comprising means to carry a plurality of reagent-storing disposable chemical testing containers; means to transfer at least a portion of a sample from a sample storage site to a reaction compartment within one of the plurality of disposable containers; at least one means for the addition of at least one reagent stored within the disposable container to the reaction compartment forming a reaction mixture; means further along the path of travel of said carrying means to monitor at least one of the physical properties of the reaction mixture within the disposable container; said monitoring means including light source means and means responsive to the magnitude of light absorbed by the reaction mixture as light is transmitted therethrough from said light source means, said monitoring means further including means to compress said disposable container between said light source means and said responsive means during analysis to define a fixed optical path length through the reaction mixture; and means to advance said carrying means through said sample transfer and reagent addition means to said monitoring means.

2. The automated analytical apparatus of claim 1 further including means to incubate the reaction mixture within the reaction compartment of the disposable container for a period of time sufficient to bring the reaction mixture to the desired state for analysis.

3. The automated analytical apparatus of claim 1 further including means to dilute a particular sample to the appropriate concentration.

4. The automated analytical apparatus of claim 1 wherein said means to transfer sample portions includes means to dilute the sample portion to the appropriate concentration.

5. The automated analytical apparatus of claim 1 wherein said sample transfer means includes means to inject the sample into the reaction compartment of the disposable container.

6. The automated analytical apparatus of claim 1 wherein said reagent addition means includes means to place the reagent-storing chambers of the disposable container in communication with the reaction compartment.

7. The automated analytical apparatus of claim 1 further including additional reagent addition means further along the path of travel of said carrying means.

8. The automated analytical apparatus of claim 1 further including means to eject a used disposable container into a disposable zone after the disposable container has passed through the monitoring means for the last time.

9. The automated analytical apparatus of claim 1 further including additional monitoring means associated with said apparatus in said sample transfer means.

10. The automated analytical apparatus of claim 1 further including means to identify a particular disposable container as containing a sample from a particular patient and to correlate the analytical data obtained by said monitoring means with the patient identification data.

11. The automated analytical apparatus of claim 1 further including at least one additional means for the addition of at least one reagent stored within the disposable container to the reaction compartment.

12. The automated analytical apparatus of claim 1 wherein there are a plurality of monitoring means.

13. An automated analytical apparatus comprising a magazine for the storage of a plurality of different disposable reaction containers, means to add a material to be analyzed to a reaction compartment within a disposable container, at least one means for the addition of at least one reagent stored within the disposable container to the reaction compartment forming a reaction mixture, means to monitor at least one of the physical properties of the reaction mixture within the disposable container, said monitoring means including light source means and means responsive to the magnitude of light absorbed by the reaction mixture as light is transmitted therethrough from said light source means, said monitoring means further including means to compress said disposable container between said light source means and said responsive means during analysis to define a fixed optical path length through the reaction mixture; and means to transport the disposable container from said magazine through said material addition means and said reagent addition means to said monitoring means.

14. The automated analytical apparatus of claim 13 further including at least one additional means for the addition of at least one reagent stored within said disposable container to the reaction compartment.

15. An automated analytical apparatus adapted for use with reagent-storing disposable reaction containers, each of the containers being carried by a support member and being sectioned into a reaction compartment and a plurality of reagent storage compartments, the compartments being separated from each other by walls weakly bonded to the supporting carrier so that the compartments can be brought into communication upon destruction of the weak bonds; said apparatus comprising means to add a sample to be analyzed to a reaction compartment within a disposable container, at least one means for the addition of at least one reagent stored within the disposable container to the reaction compartment forming a reaction mixture, means to monitor at least one of the physical properties of the reaction mixture within the reaction compartment, said monitoring means including light source means and means responsive to the magnitude of light absorbed by the reaction mixture as light is transmitted therethrough from said light source means, said monitoring means further including means to compress said disposable container between said light source means and said responsive means during analysis to define a fixed optical path length through the reaction mixture, and means to transport the disposable container through said sample addition means and said reagent addition means to said monitoring means.

16. The automated analytical apparatus of claim 15 wherein said reagent addition means includes means to manipulate the weak bonds separating the reagent storage compartments from the reaction compartment.

17. The automated analytical apparatus of claim 16 further including means to reinforce a particular weak bond while another weak bond is being destroyed by said manipulation means.

18. The automated analytical apparatus of claim 15 further including at least one additional means for the addition of at least one reagent stored within the disposable container to the reaction compartment.

19. The automated analytical apparatus of claim 15 further including a magazine for the storage of a plurality of said disposable containers, said transport means being adapted to transport each of said disposable containers from said magazine through said sample and reagent addition means to said monitoring means.

20. An automated analytical apparatus comprising means to carry a plurality of reagent-storing, disposable chemical testing containers having at least one flexible wall; means to transfer a sample aliquot from a sample storage site to a reaction compartment within one of the plurality of disposable containers; means for the addition of at least one reagent stored within the disposable container to the reaction compartment; means further along the path of travel of said carrying means to monitor at least one of the physical properties of the reaction mixture within the reaction compartment; said monitoring means including means to cooperate with the flexible wall or walls of said reaction compartment to define a fixed optical path through the reaction mixture therein; and means to advance said carrying means through said sample transfer and reagent addition means to said monitoring means.

21. The automated analytical apparatus of claim 20 wherein said reagent addition means includes means to place the reagent-storing chambers of the disposable container in communication with the reaction compartment.

22. The automated analytical apparatus of claim 20 wherein each reagent is stored in a storage chamber separated from the reaction compartment by walls weakly bonded to a supporting carrier, and said reagent addition means includes means to manipulate the weak bonds separating the reagent storage chamber from the reaction compartment.

23. The automated analytical apparatus of claim 20 further including means to reinforce a particular weak bond separating one reagent chamber from the reaction compartment while another weak bond separating a different reagent chamber from the reaction compartment is being destroyed by said manipulation means.

24. The automated analytical apparatus of claim 20 further including at least one additional means for the addition of at least one further reagent stored within the disposable container to a reaction compartment.

25. An automated analytical apparatus comprising a magazine for the storage of a plurality of different disposable reaction containers, means to add a material to be analyzed to a reaction compartment within a disposable container, at least one means for the addition of at least one reagent stored within said disposable container to the reaction compartment forming a reaction mixture, means to monitor at least one of the physical properties of the reaction mixture within the disposable container, and means to transport the disposable container from said magazine through said material addition means and said reagent addition means to said monitoring means.

26. The automated analytical apparatus of claim 25 further including at least one additional means for the addition of at least one reagent stored within said disposable container to the reaction compartment.

27. Means to dispense a plurality of reagents from their storage sites in a disposable reaction container, each container being sectioned into a reaction compartment and a plurality of reagent storage compartments, the reaction compartment being separated from each storage compartment by a weak bond so that upon destruction of said weak bond the reaction compartment and the storage compartment can be brought into communication, said dispensing means comprising means to manipulate at least one weak bond separating a reagent storage compartment from said reaction compartment to thereby place the reagent compartment in communication with the reaction compartment, and means to reinforce at least one other of said weak bonds while said other weak bond is being destroyed by said manipulation means.

28. The means of claim 27 wherein said manipulation means comprises means to promote flexing of the opposed faces of said weak bonds.

29. The means of claim 27 wherein said manipulation means comprises means to cause one layer of said weak bond to separate from the opposing layer of said weak bond.

30. The means of claim 28 wherein said manipulation means comprises means to cause one layer of said weak bond to separate from the opposing layer of said weak bond.

31. Means to dispense a plurality of reagents from their storage sites in a disposable reaction container, each container being sectioned into a reaction compartment and a plurality of reagent storage compartments, the reaction compartment being separated from each storage compartment by a weak bond so that upon destruction of said weak bond the reaction compartment and the storage compartment can be brought into communication, said dispensing means comprising means to place at least one reagent compartment in communication with the reaction compartment and means to initially prevent such communication as to at least one other of said reagent compartments by reinforcing said weak bond adjacent thereto while said other weak bond adjacent the reagent compartment being placed in communication with the reaction compartment is being destroyed by said communication promoting means.

32. Means to dispense a plurality of reagents from their storage sites in a disposable reaction container, each container being sectioned into a reaction compartment and a plurality of reagent storage compartments, the reaction compartment being separated from each storage compartment by a weak bond so that upon destruction of said weak bond the reaction compartment and the storage compartment can be brought into communication, said dispensing means comprising means to place at least one reagent compartment in communication with the reaction compartment and means to initially prevent such communication as to at least one other of said reagent compartments by reinforcing said weak bond adjacent thereto while said other weak bond adjacent the reagent compartment being placed in communication with the reaction compartment is being destroyed by said communication promoting means.

33. An automated analytical apparatus comprising means to carry a plurality of reagent-storing, disposable chemical testing containers; means to transfer at least a portion of a sample from a sample storage site to a reaction compartment within one of the plurality of disposable containers; at least one means for the addition of at least one reagent stored within the disposable container to the reaction compartment forming a reaction mixture; means further along the path of travel of said carrying means to monitor at least one of the physical properties of the reaction mixture within the reaction compartment; and means to advance said carrying means through said sample transfer means and reagent addition means to said monitoring means.

34. The automated analytical apparatus of claim 33 including means to incubate the reaction mixture within the reaction compartment of the disposable container for a period of time sufficient to bring the reaction mixture to the desired state for analysis.

35. The automated analytical apparatus of claim 33 wherein said means to transfer sample portions includes means to dilute the sample portion added to an appropriate concentration.

36. The automated analytical apparatus of claim 33 wherein said reagent addition means includes means to place reagent-storing chambers of the disposable container in communication with the reaction compartment.

37. The automated analytical apparatus of claim 33 further including additional reagent addition means further along the path of travel of said carrying means.

38. The automated analytical apparatus of claim 33 further including means to feed a used disposable container into an output station after the disposable container has passed through the monitoring means.

39. The automated analytical apparatus of claim 33 further including additional monitoring means associated with said apparatus in said sample transfer means.

40. The automated analytical apparatus of claim 33 further including means to identify a particular disposable container as being from a particular patient and to correlate the analytical data obtained by said monitoring means with the patient identification data.

41. The automated analytical apparatus of claim 33 further including at least one additional means for the addition of at least one reagent stored within the disposable container to the reaction compartment.

42. The automated analytical apparatus of claim 33 wherein said sample transfer means includes means to inject the sample into the reaction compartment of the disposable container.

43. The automated analytical apparatus of claim 33 wherein said monitoring means includes a light source and a detection means, said detection means being positioned on the opposite side of the reaction mixture from said light source, said detection means being responsive to light transmittance of the constituents in each reaction mixture.

44. An automated analytical apparatus comprising means to carry a plurality of reagent-storing, disposable chemical testing containers; means to transfer a sample aliquot from a sample storage site to a reaction compartment within one of the plurality of disposable containers; means for the sequential addition of a plurality of reagents stored within the disposable container to the reaction compartment forming a reaction mixture; means further along the path of travel of said carrying means to monitor at least one of the physical properties of the reaction mixture within the reaction compartment; and means to advance said carrying means through said sample transfer means and reagent addition means to said monitoring means.

45. An automated analytical apparatus comprising means to carry a plurality of reagent-storing, disposable chemical testing containers; means to transfer a sample aliquot from a sample storage site to a reaction compartment within one of the plurality of disposable containers; first means for the addition of at least one reagent stored within the disposable container to the reaction compartment forming a reaction mixture; second means for the addition of at least one further reagent stored within the disposable container to the reaction compartment; means further along the path of travel of said carrying means to monitor at least one of the physical properties of the reaction mixture within the reaction compartment; and means to advance said carrying means through said sample transfer means and reagent addition means to said monitoring means.

46. An automated analytical apparatus adapted for use with reagent-storing disposable chemical testing containers, each of said containers being carried by a support member and being sectioned into a reaction compartment and a plurality of reagent storage compartments, said compartments being separated from each other by walls weakly bonded to the supporting carrier so that said compartments can be brought into communication upon destruction of the weak bonds; said apparatus comprising means to carry a plurality of said disposable containers, means to transfer a sample aliquot from a sample storage site to the reaction compartment within one of said plurality of disposable containers, at least one means for the addition of at least one reagent stored within the disposable container to the reaction compartment forming a reaction mixture, means further along the path of travel of said carrying means to monitor at least one of the physical properties of the reaction mixture within the reaction compartment, and means to advance said carrying means through said sample transfer means and reagent addition means to said monitoring means.

47. The automated analytical apparatus of claim 46 wherein said reagent addition means includes means to manipulate the weak bonds separating the reagent storage compartments from the reaction compartment.

48. The automated analytical apparatus of claim 46 further including means to reinforce a particular weak bond while another weak bond is being destroyed by said mainipulation means.

49. The automated analytical apparatus of claim 46 further including at least one additional means for the addition of at least one reagent stored within the disposable container to the reaction compartment.

50. The automated analytical apparatus of claim 46 further including a magazine for the storage of a plurality of said disposable containers, said carrying means being adapted to advance said disposable containers from said magazine through said sample and reagent addition means to said monitoring means.

51. An automated analytical system including a disposable reaction container comprising at least one compartment for the admixing of materials added thereto, a storage section having at least one separate reagent storage chamber adapted for communication with each of said admixing compartments, and restraining means to prevent the premature movement of prepackaged reagents from said storage chambers, at least a portion of said admixing compartment being sufficiently optically transparent so that said compartment can be utilized as an optical cell for optical analysis, a station for the addition of a measured quantity of a sample from a sample storage site to at least one of said admixing compartments, at least one station for the addition of at least one reagent stored within said disposable container to at least one of said admixing compartments forming a reaction mixture, a readout station for monitoring at least one of the physical properties of the reaction mixture within the admixing compartment and deriving a final analytical result based upon the information obtained therefrom, and means to route said disposable reaction container through each of said stations to said readout station.

52. The automated analytical system of claim 51 further including a second station for the addition of at least one further reagent stored within said disposable container to at least one of said admixing compartments.

53. The automated analytical system of claim 51 wherein said disposable reaction container has a single admixing compartment and a plurality of separate reagent storage chambers associated therewith, said system further including a second station for the addition of at least one further reagent stored within said disposable container to said admixing component.

54. An automated analytical system including: a disposable reaction container comprising a reaction compartment for the mixing of materials added thereto, a storage section having a plurality of separate reagent storage chambers, said reagent storage chambers being adapted to be charged with predetermined quantities of reagents, each of said reagent storage chambers being further adapted to release said reagents independently of any other reagents present in other reagent storage chambers into said reaction compartment, and means communicating with said reaction compartment for introducing a sample into said reaction compartment, at least a portion of said reaction compartment being sufficiently optically transparent so that said reaction compartment can be utilized as an optical cell for optical analysis; a station for the addition of sample to an admixing compartment; at least one station for the addition of at least one reagent stored within said disposable container to said admixing compartment forming a reaction mixture; a readout station for monitoring at least one of the physical properties of the reaction mixture within said disposable container; and means to route said disposable container through each of said stations to said readout station.

55. The automated analytical system of claim 54 further including at least one station for mixing and incubation wherein the reaction mixture is maintained within the admixing compartment of the disposable container for a period of time sufficient to bring the reaction mixture to the desired state for analysis.

56. The automated analytical system of claim 54 including a station for the dilution of a sample to be analyzed to an appropriate concentration.

57. The automated analytical system of claim 54 having a plurality of reagent addition stations.

58. The automated analytical system of claim 54 wherein said disposable container has data stored thereon.

59. An automated system for analyzing a fluid sample contained within a disposable test pack comprising: at least one sample container containing a sample fluid; at least one disposable test pack adapted to serve as an optical cuvette having a portion adapted to receive said sample fluid, a portion adapted to store at least one reagent separate from said sample fluid receiving portion, and communicating means adapted to introduce sample fluid into said sample fluid receiving portion; a filling means adapted to aliquot the sample fluid from the sample fluid container through said communicating means to said sample fluid receiving portion; reaction originating means adapted to mix at least one reagent from said reagent storage portion with said sample fluid in said test pack; means for optical measurement of the sample fluid-reagent mixture while it is in said test pack; and means to readout the measurement of the sample fluid-reagent mixture.

60. An automated analytical system for analyzing a fluid sample contained in a disposable test pack, said pack having means for receiving said sample into said pack and having at least one reagent stored within said pack but separated from said sample, said pack being sequentially passed through a plurality of processing stations comprising: a station for mixing at least one reagent stored within said pack with said fluid sample; a station for the measurement of at least one property of the sample-reagent mixture while it is in said test pack; and a station for readout of said measurement.

* * * * *